United States Patent [19]

Rice

[11] Patent Number: 4,842,259
[45] Date of Patent: Jun. 27, 1989

[54] TILTING DIAGNOSTIC TABLE

[76] Inventor: Paul Rice, c/o XRE Corporation, 300 Foster St., Littleton, Mass. 01460

[21] Appl. No.: 170,273

[22] Filed: Mar. 18, 1988

[51] Int. Cl.$^4$ ............................................. G03B 41/16
[52] U.S. Cl. ..................................... 269/323; 378/209
[58] Field of Search ................. 378/91, 196, 209, 179, 378/208; 269/322, 323

[56] References Cited

U.S. PATENT DOCUMENTS

| | | | |
|---|---|---|---|
| 4,019,059 | 4/1977 | Brundin et al. | 378/209 |
| 4,481,657 | 11/1984 | Larsson | 378/209 |
| 4,653,083 | 3/1987 | Rossi | 378/209 |

*Primary Examiner*—Robert C. Watson
*Attorney, Agent, or Firm*—M. Lawrence Oliverio

[57] ABSTRACT

An apparatus for tilting a patient supported on a diagnostic table and simultaneously maintaining a selected isocenter of the patient at a selected fixed point in space comprising a table for supporting the patient within an examination zone of a diagnostic apparatus; a vertical carriage mechanism connected to an end of the table for raising and lowering the end of the table through a predetermined range of vertical travel; a tilt pivot connecting the end of the table and the vertical carriage mechanism, for supporting the table and tilting through an arc of at least about 10 degrees; a horizontal leg mechanism movably mounted to the vertical carriage mechanism for moving the vertical carriage mechanism and the table through a predetermined range of horizontal travel; the vertical carriage mechanism being movably mounted on the horizontal leg mechanism; the horizontal leg means being movably mounted on an overhead arm mechanism; wherein the vertical carriage mechanism is movable along a vertical travel and the horizontal leg mechanism is movable along a horizontal travel sufficient to maintain the isocenter of the patient at the fixed point in space when the table is tilted around the tilt pivot.

19 Claims, 1 Drawing Sheet

TILTING DIAGNOSTIC TABLE

BACKGROUND OF THE INVENTION

In connection with the use of a variety of diagnostic apparati such as X-ray projection, NMR (nuclear magnetic resonance), and other diagnostic systems there often arises the need to focus the diagnosis on a single organ or other limited area of a patient and to conduct the diagnosis from a variety of angles without moving the diagnostic apparatus. Table apparati are typically used but suffer from various disadvantages including interference of the table apparatus with access to the patient, complexity of operation of the table and inconsistency in maintaining the localized area of the patient to be examined within the diagnostic beam or other focus of the diagnostic apparatus.

SUMMARY OF THE INVENTION

In accordance with the invention there is provided an apparatus for tilting a patient supported on a diagnostic table and simultaneously maintaining a selected isocenter of the patient at a selected fixed point in space comprising a table for supporting the patient within an examination zone of a diagnostic apparatus; a vertical carriage mechanism connected to an end of the table for raising and lowering the end of the table through a predetermined range of vertical travel; a tilt pivot connecting the end of the table and tilting the table through an arc of at least about 10 degrees; a horizontal leg mechanism movably mounted to the vertical carriage mechanism for moving the vertical carriage mechanism and the table through a predetermined range of horizontal travel; the vertical carriage mechanism being movably mounted on the horizontal leg mechanism; the horizontal leg mechanism being movably mounted on an overhead arm mechanism; wherein the vertical carriage mechanism is movable along a vertical travel and the horizontal leg mechanism is movable along a horizontal travel sufficient to maintain the isocenter of the patient at the fixed point in space when the table is tilted around the tilt pivot.

Preferably the apparatus includes a mechanism for rotating the arm mechanism, the vertical carriage mechanism, the horizontal leg mechanism, and the table around an axis intersecting the selected isocenter of the patient. The mechanism for rotating is typically connected to the overhead arm mechanism.

Preferably the apparatus includes a mechanism for automatically moving the vertical carriage mechanism and horizontal leg mechanism along vertical and horizontal displacement sufficient to compensate for the vertical and horizontal displacement of the isocenter away from the fixed point in space when the table is tilted about the tilt pivot; and, most preferably the mechanism for automatically moving includes a mechanism for simultaneously driving the vertical carriage mechanism and horizontal leg mechanism along vertical and horizontal displacements sufficient to compensate for the vertical and horizontal displacement of the isocenter away from the fixed point when the table is tilted about the tilt pivot.

Typically, the mechanism for driving includes a mechanism for directing the vertical displacement of the vertical carriage mechanism by a distance x in response to a change of an angle A in tilt of the table relative to horizontal according to the formula: $X = L \sin A$, where L is the approximate straight distance between the tilt pivot and the center of the selected isocenter; and a mechanism for directing the horizontal displacement of the horizontal leg means a distance Y in response to the change of angle A according to the formula: $Y = L - (L \cos A)$.

Most preferably the apparatus further comprises an expandable and contractable strut mechanism a selected degree; a mechanism for measuring the change of angle A of the table when the strut mechanism is expanded or contracted; and, a mechanism for inputting the change of angle A into the formulae $X = L \sin A$ and $Y = L - L \cos A$ of the mechanism for driving.

Typically the leg mechanism is slidably mounted on a first track mechanism included on the underside of the arm mechanism and the carriage mechanism is slidably mounted on a second track mechanism included on the leg mechanism, the mechanism for driving further including a first motor mechanism connected to the leg mechanism, and the leg mechanism for directing the horizontal displacement of the leg mechanism and a second motor mechanism connected to the carriage mechanism.

The leg mechanism typically includes a first roller mechanism mounted in the first track mechanism, the first roller mechanism being connected to and driven by the first motor mechanism, and the carriage mechanism typically includes a second roller mechanism mounted in the second track mechanism, the second roller mechanism being connected to and driven by the second motor mechanism. Most preferably, the mechanism for directing the vertical displacement of the vertical carriage mechanism, directs the driving by a distance X in response to a change of an angle A in tilt of the table relative to horizontal according to the formula: $X = (L \sin A) + (V \sin A \tan A/2)$; where L is the approximate straight distance between the tilt pivot and the center of the selected isocenter and V is the shortest distance between the center of the selected isocenter and the surface of the table; and, most preferably, the mechanism for directing the horizontal displacement of the horizontal leg mechanism, directs the driving by a distance Y in response to the change of angle A according to the formula: $Y = L - (L \cos A) + (V \sin A)$.

The apparatus typically further comprises an expandable and contractable strut mechanism pivotably connected to the vertical carriage mechanism and the table, a mechanism for expanding and contracting the strut mechanism a selected degree, a mechanism for measuring the change of angle A of the table when the strut mechanism is expanded or contracted, and, a mechanism for inputting the change of angle A into the formulae $X = (L \sin A) + (V \sin A \tan A/2)$ and $Y = L - (L \cos A) + (V \sin A)$ of the mechanism for driving.

The mechanism for measuring typically comprises a mechanism connected to the mechanism for expanding and contracting for converting the selected degree of expansion and contraction into the change of angle A.

BRIEF DESCRIPTION OF THE DRAWINGS

Other objects, features, and advantages will be apparent from the following detailed description of preferred embodiments taken in conjunction with the accompanying drawing in which.

DETAILED DESCRIPTION OF PREFERRED EMBODIMENTS

Figure 1:
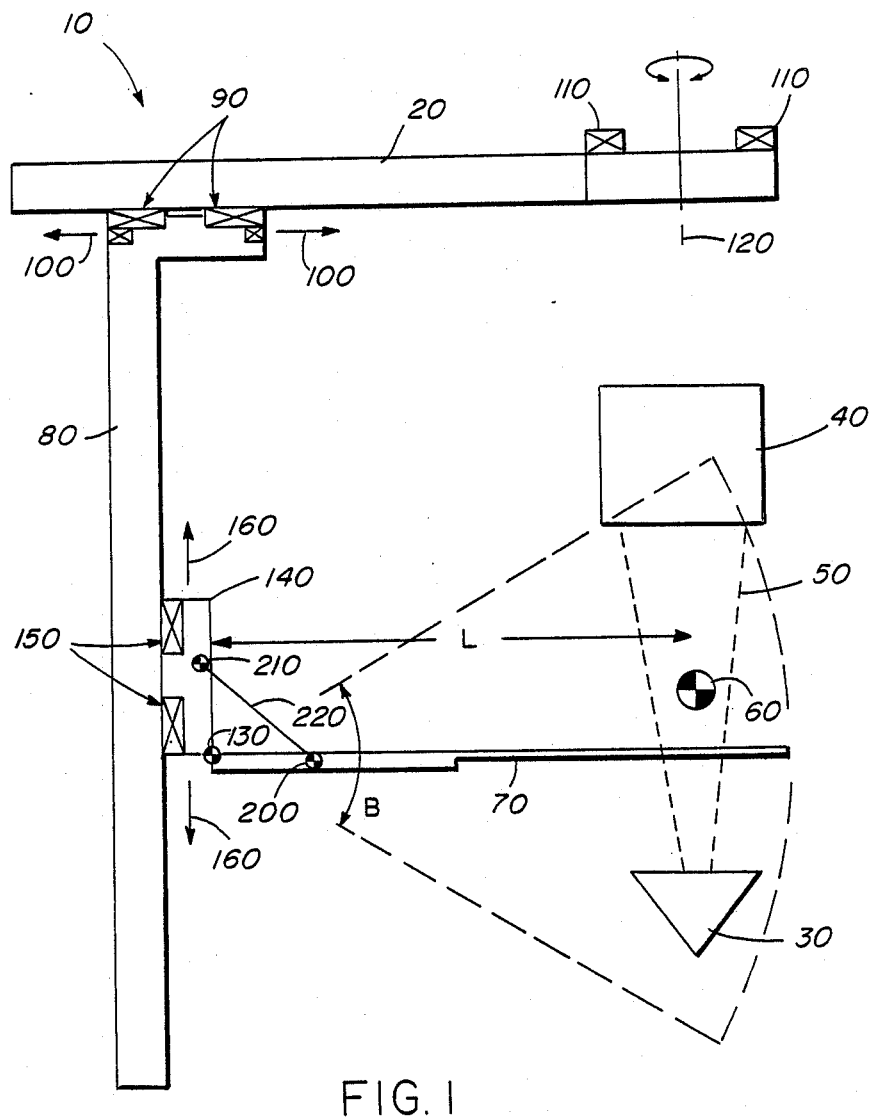
FIG. 1 is a simplified side view of a diagnostic table apparatus according to the invention; and, FIG. 2 is a simplified side view of the relative positions of the table and isocenter elements of the apparatus of the present invention before and after the table has been tilted to a selected angle.

With reference to FIG. 1, there is shown a tilting table apparatus 10 comprising a table top 70, a vertical travel carriage 140, a horizontal travel carriage or leg 80 and an overhead arm 20. The overhead arm 20 is typically mounted via a conventional rotation bearing around a central axis 120. Arm 20 extends laterally, typically horizontally, outward from axis 120 and leg 80 is typically mounted to the underside thereof within a track means (not shown) which extends the length of arm 20.

Leg 80 extends downwardly, typically vertically, from arm 20, and the vertical carriage 140 is mounted on the central axis side of surface of leg 80. Leg 80 is typically provided with a track mechanism extending the length of leg 80 and in which vertical carriage 140 is mounted.

Figure 2:
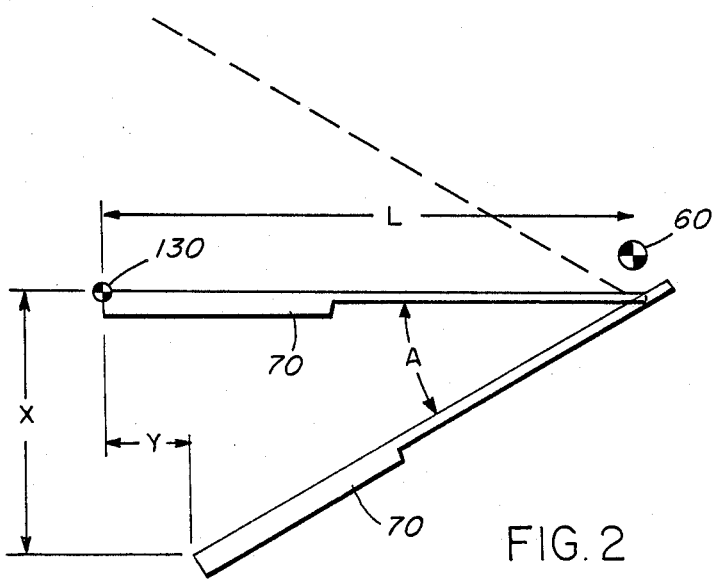

Table top 70, FIGS. 1, 2 is, in turn, pivotably mounted to vertical carriage 140 at a pivot point 130 which allows the table 70 to be pivoted through at least an angle B, typically at least about 40 degrees such that a patient (not shown) lying on top of table 70 may be tilted and examined through a variety of angles and examined with diagnostic apparatus 30, 40 without having to move the diagnostic apparatus 30, 40.

As shown in FIG. 1, a diagnostic apparatus comprising, for example, an X-ray photon beam emitter 30, emits an X-ray beam 50 having a relatively narrow and limited area/volume of focus. A detector 40, typically including an image intensifier, detects the beam 50 emitted by emitter 30. A selected area of isocenter 60 of the patient is initially positioned within the range of the beam's focus 50. As shown in FIG. 1, the table 70 is typically initially positioned horizontally such that when the apparatus 30, 40 is activated the selected isocenter 60 of the patient to be examined is located within the scope of diagnostic beam 50. Such horizontally oriented diagnosis may be insufficient for complete diagnosis. In order to effect a more complete diagnosis of the selected isocenter 60, the patient is preferably tilted around isocenter 60 by tilting table 70 around pivot point 130.

As can be seen from FIG. 1, if table 70 is simply tilted through arc B without also moving the pivoted end 130 of the table 70 a certain horizontal distance Y and vertical distance X as shown in FIG. 2, the isocenter 60 will be moved out of the diagnostic range of beam 50 and/or the table 70 (and the patient lying thereon) will collide with apparatus 30, 40.

As shown in FIG. 2, if table 70 is moved through an angle A relative to horizontal and leg 80 is moved horizontally a distance Y, and carriage 140 is moved vertically a distance X, then isocenter 60 will remain in the same point in space it was located before the table 70 was tilted, and the organ or patient area located at isocenter 60 thus remains in the diagnostic range of beam 50 after a selected change in angle A, of the table 70, all without the table 70 and patient lying thereon colliding with apparatus 30, 40.

In order to effect the horizontal and vertical displacements of leg 80, FIG. 1, and carriage 140 which are necessary to compensate for a change in angle A, FIG. 2, and maintain isocenter 60 essentially at a fixed point in space, carriage 140 and leg 80 are provided with conventional roller mechanisms 150 and 90 respectively which are driven by drive mechanisms which are programmed, mechanically or electronically, to drive roller mechanism 90 a horizontal distance Y (see FIG. 2) equal to $L-(L \cos A)$ where L is the straight distance as shown in FIGS. 1, 2 between the tilt pivot point 130 and the selected isocenter point 60 of the patient, and to drive roller mechanism 150 a vertical distance X (see FIG. 2) equal to $(L \sin A)$.

Most preferably the drive mechanisms for roller mechanism 90 are programmed to drive roller mechanism 90 a horizontal distance Y which is equal to $L-(L \cos A)+(V \sin A)$ where V is the shortest straight line distance between the center of isocenter 60 and the top surface of table 70, i.e., the distance of the center of isocenter 60 above the surface of table 70. Similarly, the drive mechanism for roller mechanism 150 is most preferably programmed to drive roller mechanism 150 a vertical distance X which is equal to $(L \sin A)+(V \sin A \tan A/2)$. In this most preferred embodiment of the invention, the horizontal and vertical displacements of the center of the isocenter 60 away from its precise initial position in space due to a change in angle A and the distance V of the isocenter 60 away from the surface of table 70 is fully accounted for. In many instances the diagnosis of the patient at various angles need not be so precise as to account for the distance V related displacements, however in many instances such precision is required; and as the distance V increases in value, such compensation for the added vertical and horizontal displacement of isocenter 60 during tilt, may be necessary to avoid collision of the patient with the diagnostic apparatus in addition to avoiding a more gross displacement of isocenter 60 from its initial position in space.

Typically table 70 is supported by a strut 220 which is pivotably connected to table 70 at a pivot point 200 and to carriage 140 at pivot point 210, FIG. 1. Strut 220 typically comprises a conventional mechanical or hydraulic strut which may be selectively and controllably expanded and/or contracted to effect a selected change in angle A, FIG. 2, of table 70 relative to horizontal.

The mechanisms for driving roller mechanisms 90 and 150, FIG. 1, are connected via conventional electronic/electromechanical mechanisms to strut 220 and typically include mechanisms for measuring any expansion and/or contraction in strut 220 and converting the measured expansion and/or contraction of strut 220 into a measurement/calculation of the change in angle A, FIG. 2, of the table 70. The driving mechanisms for roller mechanisms 90, 150 further include a conventional mechanical or electronic mechanism/program for calculating the distances X and Y, FIG. 2, according to the formulas $Y=L-(L \cos A)$ and $X=(L \sin A)$ (or $Y=L-(L \cos A)+(V \sin A)$ and $X=(L \sin A)+(V \sin A \tan A/2)$ in a most preferred embodiment) wherein the calculated change in angle A is automatically input by conventional means into the program.

The mechanism for driving roller mechanisms 90, 150 may include a manual or automatic mechanism for measuring and inputting the distance L and/or V into the program for calculating the distances X and Y. For example a manual mechanism for inputting the distances L and/or V into the program may comprise a conventional electronic keyboard connected to the program by which the user first manually measures the distances L and/or V (i.e. the distances L, FIGS. 1, 2, between the tilt pivot point 130 and the selected isocenter 60; and the distance V between the center of the selected isocenter 60 and the surface of table 70) and activates the keyboard to input the measured distances L and/or V into the program. Alternatively, the driving mechanism may include a conventional electronic mechanism which automatically establishes the distance L according to the initial horizontal position of leg 80 along the length of arm 20 at the beginning of the diagnostic cycle; and the driving mechanism further typically includes a mechanism which automatically inputs the automatically established distance L into the program for calculating X and Y. In such an automatic system where the distance L is automatically established by the initial horizontal position of leg 80 along arm 20, the position of the isocenter 60 along the length of table 70 is thus automatically established, preferably as the straight line distance L, FIGS. 1, 2 between the tilt pivot 130 and the center or axis of diagnostic beam 50. In such an automatic system for establishing the distance L, the user may therefore automatically establish the isocenter 60 of the patient by simply initially positioning leg 80, at a selected initial position along the length of arm 20 whereby a selected isocenter area 60 of a patient lying on table 70 is centered within diagnostic beam 50.

Arm 20 is most preferably rotatably mounted on an axis 120 which defines the axis of the isocenter 60; where axis 120 defines the axis of the isocenter 60, the diagnostic machine elements 30, 40 must be positioned beneath arm 20 such that the axis of beam volume/area 50, FIG. 1, is aligned with axis 120.

In an automatic system as described above where the distance L, FIGS. 1, 2 is established according to the initial diagnostic position established as having an axis which is coincident with axis 120. In such a preferred automatic system, the axis of the diagnostic beam 50 is aligned with axis 120 and thus the user must take care to insure that the center/axis of the selected isocenter area 60 of the patient lying on table 70 is aligned with axis 120. In a most preferred system, the center of the diagnostic beam 50 is initially aligned with axis 120. Roller mechanisms 90 and 150, FIG. 1, are preferably driven by conventional motor mechanisms which are in turn connected to and directed by a conventional computer/computer program to drive leg 80 and carriage 140 according to the formulae $Y = L - (L \cos A)$ and $X = (L \sin A)$ (or $Y = L - (L \cos A) + (V \sin A)$ and $X = (L \sin A) + (V \sin A \tan A/2)$ in a most preferred embodiment) along the track mechanisms provided on arm 20 and leg 80 respectively. A conventional mechanism for measuring the degree of contraction and/or 220 and the computer/computer program, and the computer/computer program preferably includes a program for calculating/converting the measured degree of expansion/contraction of strut 220 into the angle of tilt A, FIG. 2. The computer/computer program also preferably includes a conventional mechanism for automatically inputting such calculated angle A into the algorithms $Y = L - (L \cos A)$ and $X = (L \sin A)$ (or $Y = L - (L \cos A) + (V \sin A)$ and $X = (L \sin A) + (V \sin A \tan A/2)$ in a most preferred embodiment).

As described above the computer/computer program which directs the drive of the motor mechanism(s) which drive roller mechanisms 90, 150, FIG. 1, may include a mechanism connected to a conventional keyboard or other mechanism which allows the user to manually input manually measured distances L and/or V into the algorithms $Y = L - (L \cos A)$ and $X = (L \sin A)$ (or $Y = L - (L \cos A) + (V \sin A)$ and $X = (L \sin A) + (V \sin A \tan A/2)$ in a most preferred embodiment).

Alternatively, in a fully automatic system, there may be provided a conventional monitor mechanism which monitors the horizontal position/displacement of leg 80 along arm 20 at the beginning of the diagnostic cycle. Such a monitor mechanism is preferably connected to the computer/computer program which may include a predetermined program/algorithm for calculating the distance L from the initial monitored position of leg 80 and automatically inputs the calculated distance L into the programs $Y = L - (L \cos A)$ and $X = (L \sin A)$ (or $Y = L - (L \cos A) + (V \sin A)$ and $X = (L \sin A) + (V \sin A \tan A/2)$ in a most preferred embodiment).

Most preferably the computer/computer program which directs the drive mechanisms which drive roller mechanisms 90, 150, FIG. 1, begin directing the drive mechanisms to drive leg 80 and carriage 140 as soon as and simultaneously with the tilting of table 70. For example as table 70 begins tilting and/or changing its angle relative to horizontal by a change of angle A, the drive mechanisms are simultaneously directed to drive leg 80 and carriage 140 by horizontal and vertical distances of $Y = L - (L \cos A)$ and $X = (L \sin A)$ (or $Y = L - (L \cos A) + (V \sin A)$ and $X = (L \sin A) + (V \sin A \tan A/2)$ in a most preferred embodiment).

A conventional measuring mechanism may be connected to strut 220, which measures the degree of expansion and/or contraction of strut 220. Preferably the strut measuring mechanism automatically inputs such measured degree of contraction/expansion of strut 220 into the computer/computer program which preferably includes a program which calculates the degree of change of the angle A of table 70. The specific program/algorithm for calculating A depends on the precise positioning of pivot attachment points 210 and 200 relative to pivot point 130. The mechanism for measuring the contraction/expansion of strut 220 typically measures such contraction/expansion in increments of at least about 0.5 inches and the measuring mechanism preferably inputs such measured incremental changes in the degree of strut 220 contraction/expansion automatically into the program/algorithm which calculates A. The program(s)/algorithm(s) for calculating Y and X typically include a mechanism for automatically inputting the calculated change in angle A thereinto. Typical mechanisms for measuring the change in angle A are conventional optical recorders, potentiometers and the like. Most preferably the mechanism selected for measuring the change in angle A and/or the change in angle A and/or the change in the length of strut 220 is capable of measuring such changes in increments of at least 0.5 degrees and/or at least 0.5 inches in length.

Most preferably the computer/computer program which directs the drive mechanism for roller mechanisms 90, 150, FIG. 1, includes all of the programs/algorithms described herein including the programs/algorithms for calculating Y, X and A; and all such programs(s)/algorithm(s) are interconnected in conventional electronic manner for automatic input/output of the various calculated variables such as X, Y, A and the degree of expansion/contraction of strut 220.

The strut 220 typically includes a conventional control mechanism for selectively expanding and/or contracting the strut 220 thereby allowing the user to selectively tilt and/or change the angle of the table to or by any selected angle A, FIG. 2. In such a system the control mechanism for expanding/contracting the strut 220 may be pre-calibrated to effect a given tilt angle A for a given strut 220 expansion/contraction. Where a control mechanism is provided for selectively choosing a selected tilt angle A or expansion/contraction, such a control mechanism may be connected directly to the computer/computer program for direct input of the selected pre-calibrated tilt angle A into the $Y=L-(L \cos A)+(V \sin A)$ and $X=(L \sin A)+(V \sin A \tan A/2)$ strut expansion/contraction into the predetermined strut expansion/contraction into the predetermined program/algorithm for calculating the tilt angle A from the degree of selected expansion/contraction. In an alternative embodiment the change in angle A of the table may be measured independently of the strut or other mechanism which physically performs the tilting of the table. For example an optical encoder, mechanical angle measuring device, or other angle measuring device may be employed. In all embodiments, the change in angle A once measured is input by conventional means included in the drive mechanisms which direct the horizontal X and Y displacements of the horizontal leg 80 and vertical carriage, FIGS. 1 and 2.

It will now be apparent to those skilled in the art that other embodiments, improvements, details and uses can be made consistent with the letter and spirit of the foregoing disclosure and within the scope of this patent, which is limited only by the following claims, construed in accordance with the patent law, including the doctrine of equivalents.

What is claimed is:

1. Apparatus for tilting a patient supported on a diagnostic table and simultaneously maintaining a selected isocenter of the patient at a selected fixed point in space comprising:

a table for supporting the patient within an examination zone of a diagnostic apparatus;

vertical carriage means connected to an end of the table for raising and lowering the end of the table through a predetermined ranged of vertical travel;

a tilt pivot connecting the end of the table and the vertical carriage means, for supporting the table and tilting the table through an arc of at least about 10 degrees;

a horizontal leg means movably mounted to the vertical carriage means for moving the vertical carriage means and the table through a predetermined range of horizontal travel;

the vertical carriage means being movably mounted on the horizontal leg means;

the horizontal leg means being movably mounted on an overhead arm means;

wherein the vertical carriage means is movable along a vertical travel and the horizontal leg means is movable along a horizontal travel sufficient to maintain the isocenter of the patient at the fixed point in spaced when the table is tilted around the tilt pivot;

the apparatus further comprising means for rotating the arm means, the vertical carriage means, the horizontal leg means, and the table around an axis intersecting the selected isocenter of the patient.

2. The apparatus of claim 1 wherein the means for rotating is connected to the overhead arm means.

3. The apparatus of claim 2 further comprising means for automatically moving the vertical carriage means and horizontal leg means along vertical and horizontal displacements sufficient to compensate for the vertical and horizontal displacement of the isocenter away from the fixed point when the table is tilted about the tilt pivot.

4. Apparatus for tilting a patient supported on a diagnostic table and simultaneously maintaining a selected isocenter of the patient at a selected fixed point in space comprising:

a table for supporting the patient within an examination zone of a diagnostic apparatus;

vertical carriage means connected to an end of the table for raising and lowering the end of the table through a predetermined range of vertical travel;

a tilt pivot connecting the end of the table and the vertical carriage means, for supporting the table and tilting the table through an arc of at least about 10 degrees;

a horizontal leg means movably mounted to the vertical carriage means for moving the vertical carriage means and the table through a predetermined range of horizontal travel;

the vertical carriage means being movably mounted on the horizontal leg means;

the horizontal leg means being movably mounted on an overhead arm means;

wherein the vertical carriage means is movable along a vertical travel and the horizontal leg means is movable along a horizontal travel sufficient to maintain the isocenter of the patient at the fixed point in space when the table is tilted around the pivot;

the apparatus further comprising means for automatically moving the vertical carriage means and horizontal leg means along vertical and horizontal displacement sufficient to compensate for the vertical and horizontal displacement of the isocenter away from the fixed point in space when the table is tilted about the tilt pivot.

5. The apparatus of claim 2 wherein the means for automatically moving includes means for simultaneously driving the vertical and horizontal leg means along vertical and horizontal displacements sufficient to compensate for the vertical and horizontal displacement of the isocenter away from the fixed point when the table is tilted about the tilt pivot.

6. The apparatus of claim 4 wherein the means for automatically moving includes means for simultaneously driving the vertical carriage means and horizontal leg means along vertical and horizontal displacements sufficient to compensate for the vertical and horizontal displacement of the isocenter away from the fixed point when the table is tilted about the tilt pivot.

7. The apparatus of claim 5 wherein the means for driving includes:

means for directing the vertical displacement of the vertical carriage means by a distance X in response to a change of an angle A in tilt of the table relative to horizontal according to the formula: $X=L(\sin A)$, where L is the approximate straight distance between the tilt pivot and the center of the selected isocenter; and, means for directing the horizontal displacement of the horizontal leg means a distance Y in response to the change of angle A according to the formula: $Y=L-(L \cos A)$.

8. The apparatus of claim 4 wherein the means for driving includes:

means for directing the vertical displacement of the vertical carriage means by a distance X in response to a change of angle A in tilt of the table relative to horizontal according to the formula: $X=(L \sin A)$, where L is the approximate straight distance between the tilt pivot and the center of the selected isocenter; and, means for directing the horizontal displacement of the horizontal leg means a distance Y in response to the change of angle A according to the formula: $Y=L-(L\cos A)$.

9. The apparatus of claim 7 further comprising:

an expandable and contractable strut means pivotably connected to the vertical carriage means and the table;

means for expanding and contracting the strut means a selected degree;

means for measuring the change of angle A of the table when the strut means is expanded or contracted; and, means for inputting the change of angle A into the formulae: $X=(L\sin A)$ and $Y=L-(L\cos A)$ of the means for driving.

10. The apparatus of claim 8:

an expandable and contractable strut means pivotably connected to the vertical carriage means and the table;

means for expanding and contracting the strut means a selected degree;

means for measuring the change of angle A of the table when the strut means is expanded or contracted; and, means for inputting the change of angle A into the formulae: $X=(L\sin A)$ and $X=L-(L\cos A)$ of the means for driving.

11. The apparatus of claim 9 wherein the leg means is slidably mounted on a first track means included on the underside of the arm means and the carriage means is slidably mounted on a second track means included on the leg means, the means for driving further including a first motor means connected to the leg means and the means for directing the horizontal displacement of the leg means, and a second motor means connected to the carriage means and the means for directing the vertical displacement of the carriage means.

12. The apparatus of claim 10 wherein the leg means is slidably mounted on a first track means include on the underside of the arm means and the carriage means is slidably mounted on a second track means included on the leg means, the means for driving further including a first motor means connected to the leg means and the means for directing the horizontal displacement of the leg means, and a second motor means connected to the carriage means and the means for directing the vertical displacement of the carriage means.

13. The apparatus of claim 11 wherein the leg means includes first roller means mounted in the first track means, the first roller means being connected to and driven by the first motor means, and wherein the carriage means includes second roller means mounted in the second track means, the second roller means being connected to and driven by the second motor means.

14. The apparatus of claim 12 wherein the leg means includes first roller means mounted in the first track means, the first roller means being connected to and driven by the first motor means, and wherein the carriage means includes second roller means mounted in the second track means, the second roller means being connected to and driven by the second motor means.

15. The apparatus of claim 5 wherein the means for driving includes:

means for directing the vertical displacement of the vertical means by a distance X in response to a change of an angle A in tilt of the table relative to horizontal according to the formula: $X=(L\sin A)+(V\sin A\tan A/2)$; where L is the approximate straight distance between the tilt pivot and the center of the selected isocenter and V is the shortest distance between the center of the selected isocenter and the surface of the table; and, means for directing the horizontal displacement of the horizontal leg means a distance Y in response to the change of angle A according to the formula: $Y=L-(L\cos A)+(V\sin A)$.

16. The apparatus of claim 6 wherein the means for driving includes:

means for directing the vertical displacement of the vertical carriage means by a distance X in response to a change of an angle A in tilt of the table relative to horizontal according to the formula: $X=(L\sin A)+(V\sin A\tan A/2)$; where L is the approximate straight distance between the tilt pivot and the center of the selected isocenter and V is the shortest distance between the center of the selected isocenter and the surface of the table; and, means for directing the horizontal displacement of the horizontal leg means a distance Y in response to the change of angle A according to the formula: $Y=L-(L\cos A)+(V\sin A)$.

17. The apparatus of claim 15 further comprising:

an expandable and contractable strut means pivotably connected to the vertical carriage means and the table;

means for expanding and contracting the strut means a selected degree;

means for measuring the change of angle A of the table when the strut means is expanded or contracted; and, means for inputting the change of angle A into the formulae: $X=(L\sin A)+(V\sin A\tan A/2)$ and $Y=L-(L\cos A)+(V\sin A)$ of the means for driving.

18. The apparatus of claim 16 further comprising:

an expandable and contractable strut means pivotably connected to the vertical carriage means and the table;

means for expanding and contracting the strut means a selected degree;

means for measuring the change of angle A of the table when the strut means is expanded or contracted; and, means for inputting the change of angle A into the formulae: $X=(L\sin A)+(V\sin A\tan A/2)$ and $Y=L-(L\cos A)+(v\sin A)$ of the means for driving.

19. The apparatus of claims 9, 10, 17 of 18 wherein the means for measuring comprises a means connected to the means for expanding and contracting for converting the selected degree of expansion and contraction into the change of angle A.

* * * * *